United States Patent [19]

Jones et al.

[11] Patent Number: 5,339,025
[45] Date of Patent: Aug. 16, 1994

[54] METHOD FOR DETERMINING THE GRANULAR NATURE OF SUPERCONDUCTORS USING PULSED CURRENT

[75] Inventors: Thomas E. Jones, Spring Valley; Wayne C. McGinnis, San Diego, both of Calif.

[73] Assignee: The United States of America as represented by the Secretary of the Navy, Washington, D.C.

[21] Appl. No.: 10,685

[22] Filed: Jan. 28, 1993

[51] Int. Cl.⁵ ............................................. G01N 27/00
[52] U.S. Cl. .................................. 324/71.6; 324/713; 505/843
[58] Field of Search ...................... 324/71.6, 248, 713, 324/715, 717, 719; 505/726, 843

[56] References Cited

U.S. PATENT DOCUMENTS

| | | | |
|---|---|---|---|
| 3,390,330 | 6/1968 | Meyerhoff et al. | 324/117 R |
| 3,428,891 | 2/1969 | Purcell et al. | 324/717 |
| 4,213,087 | 7/1980 | English et al. | 324/719 |
| 4,777,437 | 10/1988 | Tashiro et al. | 324/248 |
| 4,904,929 | 2/1990 | Bohandy et al. | 324/71.6 |
| 4,947,118 | 8/1990 | Fujimaki | 324/248 |
| 5,065,087 | 11/1991 | Kita et al. | 324/71.6 |
| 5,134,360 | 7/1992 | Martin et al. | 324/71.6 |
| 5,223,798 | 6/1993 | McGinnis et al. | 324/713 |

OTHER PUBLICATIONS

"Critical Current Measurements on Yb–Ba–Cu–O" by T. E. Jones et al., Materials Research Society Extended Abstracts, High Temperature Superconductors, Proceedings of Symposium S, Apr. 1987, pp. 235–237.
"Pulsed Current Measurement of the Resistive Transition and Critical Current in High $T_c$ Superconductors" by W. C. McGinnis et al.; Rev. Sci. Instrum. 61(3) Mar. 1990, pp. 984–987.
"Critical Currents and Current–Voltage Characteristics in Superconducting Ceramic $YBa_2Cu_3O_7$" by Dan Goldschmidt, Physical Review, vol. 39, No. 13, May 1, 1989, pp. 9139–9146.
"Critical Current Densities For the High Temperature Ceramic Superconductors $YBa_2Cu_3O_7$ and $Bi_2Sr_2Ca_2Cu_3O_{10}$" by W. C. McGinnis et al., IEEE Transactions on Magnetics, vol. 25, No. 2, Mar. 1989, pp. 2138–2141.

Primary Examiner—Kenneth A. Wieder
Assistant Examiner—Christopher M. Tobin
Attorney, Agent, or Firm—Harvey Fendelman; Thomas Glenn Keough; Michael A. Kagan

[57] ABSTRACT

The present invention provides a method for determining the granular nature of superconductive materials and devices which includes the steps of: conducting a substantially rectangular current pulse through the superconductive material, maintaining the temperature of the superconductive material at a substantially constant temperature which does not exceed the critical temperature of the superconductive material; determining the amplitude of the current pulse; determining the electrical resistance, R, of the superconductive material resulting from conducting current pulse through the superconductive material; increasing the current until the electrical resistance of the superconductive material becomes saturated; determining the electrical resistance difference, $\delta$, between the electrical resistance, R, of the saturated superconductive material and a total normal state electrical resistance of the superconductive material; generating a first output signal if $|\delta| \leq \epsilon$, where $\epsilon$ represents a predetermined limit, where the first output signal corresponds to the superconductive material having a homogenous microscopic morphology; and generating a second output signal if $|\delta| > \epsilon$, where the second output signal corresponds to the superconductive material having a granular morphology. The method may also be used to determine the saturated electrical resistances of the superconductive sample.

9 Claims, 3 Drawing Sheets

5,339,025

METHOD FOR DETERMINING THE GRANULAR NATURE OF SUPERCONDUCTORS USING PULSED CURRENT

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to the field of superconductors and more particularly, to a method for determining the granular nature of superconductors. A superconductor is a material that loses all electrical resistance to the passage of DC electric current below some temperature referred to as the critical temperature, $T_c$. That is, while superconducting, there is no dissipation of energy; the electrical conduction is lossless. A superconductor only remains superconducting, however, below its critical temperature, below some critical applied magnetic field, and only for electric currents below some critical current density. If the critical current density is too low, the suitability of such material for practical applications may be very limited.

Superconducting materials are useful because their critical current density, $J_c$, can be very large—over 1,000,000 Amps/cm$^2$. Because superconductors can carry such high current densities, superconducting materials formed into wires can generate magnetic fields many times that of the largest iron electromagnets, and they can do so in a package small enough to be held in the palm of one's hand. Superconductors have many applications in electronics. For example, superconducting quantum interference devices (SQUIDs) may be used to make ultra-sensitive magnetometers and gradiometers, digital logic and memory circuits, and radiation detectors. Also, superconducting interconnects, in the form of superconducting thin films, on microelectronic packages and chips can be used to reduce electrical resistance losses and dispersion for a diverse mix of microelectronic circuits. The actual current needed for these applications is usually in the range of milliamps rather than kiloamps. However, the trend in microelectronic design is size reduction. Hence, the required current densities for many microelectronic applications are actually comparable to those required for large scale applications such as motors, generators, and energy storage systems. Thus, if superconducting films cannot carry appreciable electric current densities, they will not be very useful for most microelectronic circuits.

In 1987, high temperature ceramic superconductors were discovered. These materials are very different than previously known superconductors, such as niobium (Nb), niobium-titanium (Nb-Ti), and niobium germanium (Nb$_3$Ge), because they are superconducting at much higher and more easily attained temperatures. The earlier materials mentioned above had transition temperatures in the range of 9–23K and generally required liquid helium cooling. The term high-temperature superconductors refers to materials with transition temperatures greater than the boiling point of liquid nitrogen, which is approximately 77K at atmospheric pressure. These new materials can, therefore, be cooled with liquid nitrogen rather than with liquid helium. The advantage of cooling a superconducting material below its critical temperature with liquid nitrogen rather than with liquid helium is that liquid helium is twenty to forty times more costly than liquid nitrogen, and liquid nitrogen is much easier to handle than is liquid helium.

Unlike previously known superconducting materials, the new ceramic superconductors commonly have two different critical currents that differ widely in magnitude. This characteristic of ceramic superconductors was not universally appreciated in the scientific community during the 1987–1988 time period. Reports of critical current measurements performed on the same high-$T_c$ compound differed widely around the world, depending on who reported the results, the type of samples used, and most notably, the measurement techniques employed. For example, sintered ceramic samples had vastly different transport critical currents than epitaxial thin films. Even for a specific sample of high-$T_c$ material, such as a sintered fragment, the critical current determined from a transport measurement might be vastly different from the critical current inferred from a magnetization measurement. Many different techniques have been developed over the years in order to measure the critical current density of superconducting materials. For conventionally known materials, it really did not matter a great deal which of the known measurements technique was used because conventional superconductive materials usually have only one critical current density.

However, the new ceramic superconductors are commonly characterized as having two different critical current densities because of their unique microscopic granular morphology. Such granular morphology results from the way the materials are synthesized, and from the complexity of the fundamental compounds. The manufacture of ceramic superconductors may result in the formation of multiple crystallographic phases, as well as non-superconducting or poorly superconducting regions consisting of impurities, unreacted constituents, and reaction by-products. In a material having a microscopic granular morphology, high quality grains of material having the capability of behaving as a good superconductor are separated by lower quality, non-superconducting or weakly superconducting material. Such lower quality materials are referred to as "weak-links". The weak-links can conduct only relatively low levels of current. The weak-link intergrain regions may consist of materials that are off-stoichiometry, under-oxygenated, or which contain impurities and reaction by-products. Transport techniques, which measure $J_c$ by passing a DC electric current through the superconducting material or device, are thereby limited to measuring the lower critical current which defines the weak-link or intergrain critical current density. Referring to FIG. 1, there is shown a representation of a cross-sectional area of a granular superconducting material "E" comprised of high quality superconductive grains "F" that can carry large currents which are connected by intergranular regions "G." The lines "H" represent current paths through the superconducting material. In order to traverse the superconducting material "E," electrical current must pass through poorer intergranular regions "G" that can only carry much less current.

Non-transport methods for determining the current-carrying capacity of superconductors, such as by studying the magnetic hysteresis exhibited by such materials, can be used to infer the intrinsic critical current density in the individual grains (intragranular critical current density). Discrepancies in the reported critical currents of ceramic superconducting materials due to the fact these types of materials characteristically exhibit two critical currents resulted in much confusion and a lack of progress toward developing practical applications for these materials.

For most applications, the existence of two critical current densities for ceramic superconductors is an indication of materials defects which may limit the performance of the superconductor. Ideally, there should be just one, large critical current for a given material. That is, for a well prepared sample of ceramic superconductor, measurements of the weak-link, intergranular critical current, and of the intrinsic, intragranular critical current should yield the same value, indicating that there are no intergranular regions limiting the current-carrying capacity of the superconducting material or device.

The standard technique for determining the critical current, $I_c$, of a superconductor consists of applying a constant direct current, I, until the voltage difference, V, which appears across the superconducting material or device exceeds a given value. The current associated with this voltage difference is operationally defined as the critical current. That is, until the critical current is exceeded, the voltage drop, V, across the superconducting sample is zero to within the limit of experimental error. The value of the critical current, $I_c$, determined from such an experiment can depend on the voltage (or electric field or resistance) criterion chosen. This DC method, although widely used, has the following drawbacks: (1) $I^2r$ heating of the sample and contacts (with a total resistance, R) can give a misleadingly low value for $I_c$; (2) no information is obtained on the rest of the superconducting-to-normal transition, only on the onset of resistance, and (3) special sample mounts (heavy wires, etc.) are needed to carry the large direct currents involved in measurements on bulk superconducting materials or devices.

With regard to item (2) in the immediately preceding paragraph, the standard DC technique yields only the lower value of the critical current, if there is more than one, because the heat generated when $I_c$ is exceeded heats the entire sample, driving it normal. This is the reason no information is obtained on the rest of the superconducting-to-normal transition by use of this technique. In applying the standard techniques, one could not determine whether the superconducting device under test is homogeneous but of poor quality, or whether it might have higher quality grains embedded in a poor quality matrix.

U.S. Pat. No. 5,223,798, entitled "Method for Measuring the Resistive Transition and Critical Current in Superconductors Using Pulsed Current," incorporated herein by reference, describes a method for measuring both of the critical currents of granular superconductors directly at the same time. Briefly, the technique employs short pulses of constant current to probe the conductivity of the superconducting material or device. The pulses have a duty cycle sufficiently low to minimize the power input to the superconducting material or device even when parts of the superconducting material or device have been driven normal by exceeding a local critical current. Because of the nature of the current pulses, this method is referred to as a pulsed-DC technique. The pulsed-DC technique provides a repeatable method for determining the different critical currents of a high temperature superconducting material such as a ceramic superconductor.

Just as there are two characteristic critical current densities for a granular superconductor, there are also two characteristic normal state resistances. The normal state resistance, $R_N$, of a superconductive material is the electrical resistance of the material when it is in the normal, or non-superconducting, state. In the normal, non-superconductive state, superconductivity is completely destroyed, even on a microscopic level. This would be the case, for example, if the temperature of the material exceeds the $T_c$ of every component of the material. In a granular superconductor, the grains (high quality superconductor) and the weak-links between grains (poor superconductor or non-superconductor) each have their own unique resistance value. Such resistances may be referred to as the intergranular (between grains) normal state resistance, $R_{inter}$, and the intragranular (within a grain) normal state resistance, $R_{intra}$. The total normal state resistance, $R_{total}$, of a granular superconductive material is $(R_{intra}+R_{inter})$. Thus, there is a need for a reliable method for determining and comparing the component resistances $R_{intra}$ and $R_{inter}$ with the total normal state resistance, $R_{total}$, of a superconductor in order to determine the granular nature of the superconductor.

SUMMARY OF THE INVENTION

Figure 1:
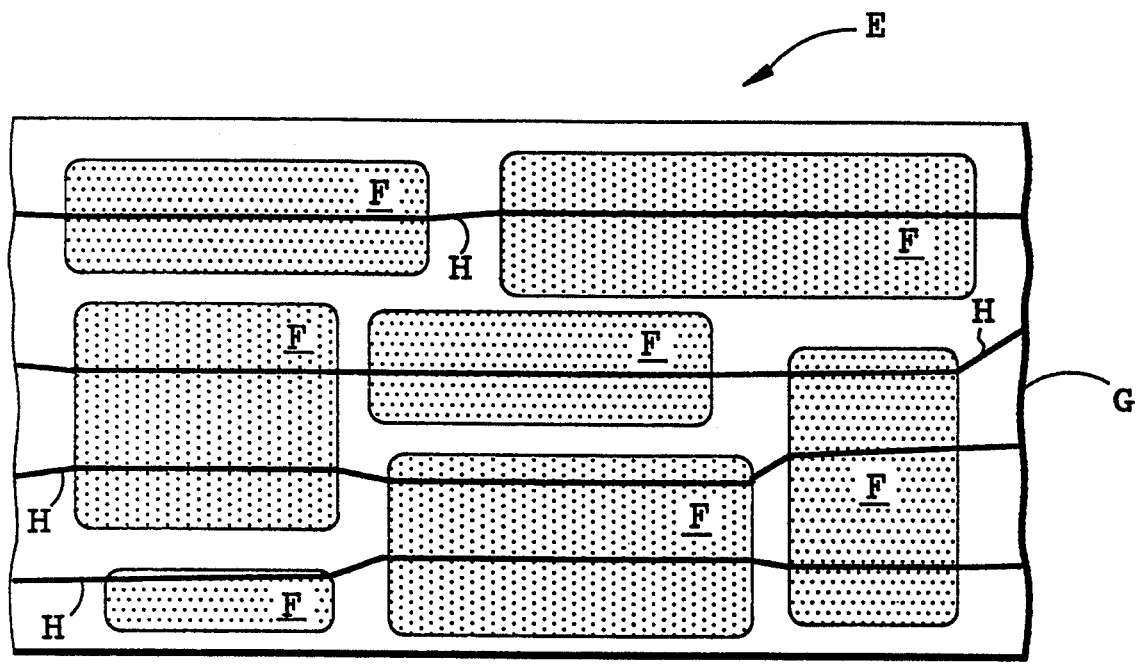
FIG. 1 is a schematic cross-sectional view of a typical granular superconductor.

The present invention provides a method for determining the granular nature of a superconductor by determining if the superconductor has one or two normal state resistances. In accordance with the method of the present invention, the detection of two normal state resistances of a superconductor indicates that the superconductor has a granular morphology, whereas detection of only one normal state resistance indicates that the superconductor has a homogeneous morphology. The granular nature of a superconductor may therefore, for example, be determined by measuring the intergranular or intragranular normal state resistance and comparing it to the known or determined total normal state resistance. The terms "superconductive material" and "superconductor" refer to materials which are superconducting when such materials are subjected to appropriate combinations of temperature, magnetic field, and current density. Critical values of temperature, magnetic field, and current density exist below which a superconductive material is in the superconducting state, and above which it is in the normal, or non-superconducting, state.

One implementation of the present invention provides a method for determining the granular nature of a superconductive material (the sample) by comparing the determined normal state resistance and the known total normal state resistance of the material. One implementation of the invention includes the steps of: conducting a substantially rectangular current pulse through the superconductive material; maintaining the temperature of the superconductive material at a substantially constant temperature which does not exceed the critical temperature of the superconductive material; determining the amplitude of the current pulse; determining the electrical resistance, R, of the superconductive material resulting from conducting current pulse through the superconductive material; increasing the current until the electrical resistance of the superconductive material becomes saturated; determining the electrical resistance difference, $\delta$, between the saturated electrical resistance, $R_1$, of the saturated superconductive material and the known total normal state electrical resistance of the superconductive material; generating a first output signal if $|\delta| \leq \epsilon$, where $\epsilon$ represents a predetermined limit, where the first output signal corresponds to the superconductive material having a homogenous microscopic morphology; and generating a second output signal if $|\delta| > \epsilon$, where the second output signal corresponds to the superconductive material having a granular morphology. The method may also be used to determine the saturated electrical resistances of the superconductive sample, in cases where more than one exist.

Another implementation of the invention includes the steps of: conducting a substantially rectangular current pulse through the superconductive material; maintaining the temperature of the superconductive material at a substantially constant temperature which does not exceed the critical temperature of the superconductive material; determining the amplitude of the current pulse; determining the electrical resistance of the superconductive material resulting from conducting current pulse through the superconductive material; increasing the amplitude of the current pulse until the electrical resistance of the superconductive material becomes saturated at a first saturated electrical resistance, $R_1$; further increasing the amplitude of the current pulse until the electrical resistance of the superconductive material increases from the first saturated electrical resistance, $R_1$, to a second saturated electrical resistance, $R_2$, the second saturation electrical resistance being equal to the total normal state electrical resistance; determining an electrical resistance difference, $\delta$, between $R_1$ and $R_2$; generating a first output signal if $|\delta| \leq \epsilon$, where $\epsilon$ represents a predetermined limit, where the first output signal corresponds to the superconductive material having a homogenous morphology; and generating a second output signal if $|\delta| > \epsilon$, where the second output signal corresponds to the superconductive material having a granular morphology.

The method of the present invention may be employed to determine the granular nature, or morphology, of superconducting components such as wires, films, and bulk components. In some applications of superconducting materials, such as in infrared detectors, a particular type of granular morphology may be desired and necessary for the proper operation of the device. Therefore, the method of the present invention may be used to verify the appropriate morphology of the superconductor for a given application. The method of the present invention also is expected to find wide application in the determination of the quality of high-temperature ceramic superconducting materials.

An important advantage of the method of the present invention is in providing a simple electronic diagnostic procedure for determining whether a superconductive material has a homogeneous or granular composition.

DESCRIPTION OF THE PREFERRED EMBODIMENT

The present invention employs a pulsed-DC method in which current is conducted at low frequency in one or more short pulses through a sample of a material in a superconducting state which is to have the nature of its morphology determined, i.e., whether such morphology is granular or homogenous. Generally, in the implementation of the present invention, a voltage difference, V, is measured across a superconducting sample while short pulses of current having an amplitude, I, are conducted through the material comprising the sample. The sample resistance, R, is given by Ohm's law, $R = V/I$. The heat generated in the superconducting sample as a result of the current pulses is preferably minimized such that the sample temperature does not increase by more than about 1K (compared to the temperature the sample would be at with no current pulses being conducted through the sample). The sample may be maintained at a suitable temperature below its critical temperature, $T_c$, by preferably immersing it in a cryogenic liquid, such as liquid nitrogen, or by mounting the sample in good thermal contact with a metal block which is much more massive than the sample and is cooled to a temperature low enough to maintain the sample below its critical temperature. The minimization of sample heating is particularly important for very small samples having current contacts in close thermal proximity to the voltage contacts on the sample. Minimization of sample heating is also important for measurements (such as the temperature dependence of $I_c$) in which the superconducting sample may not be immersed in a liquid cryogen.

Figure 2:
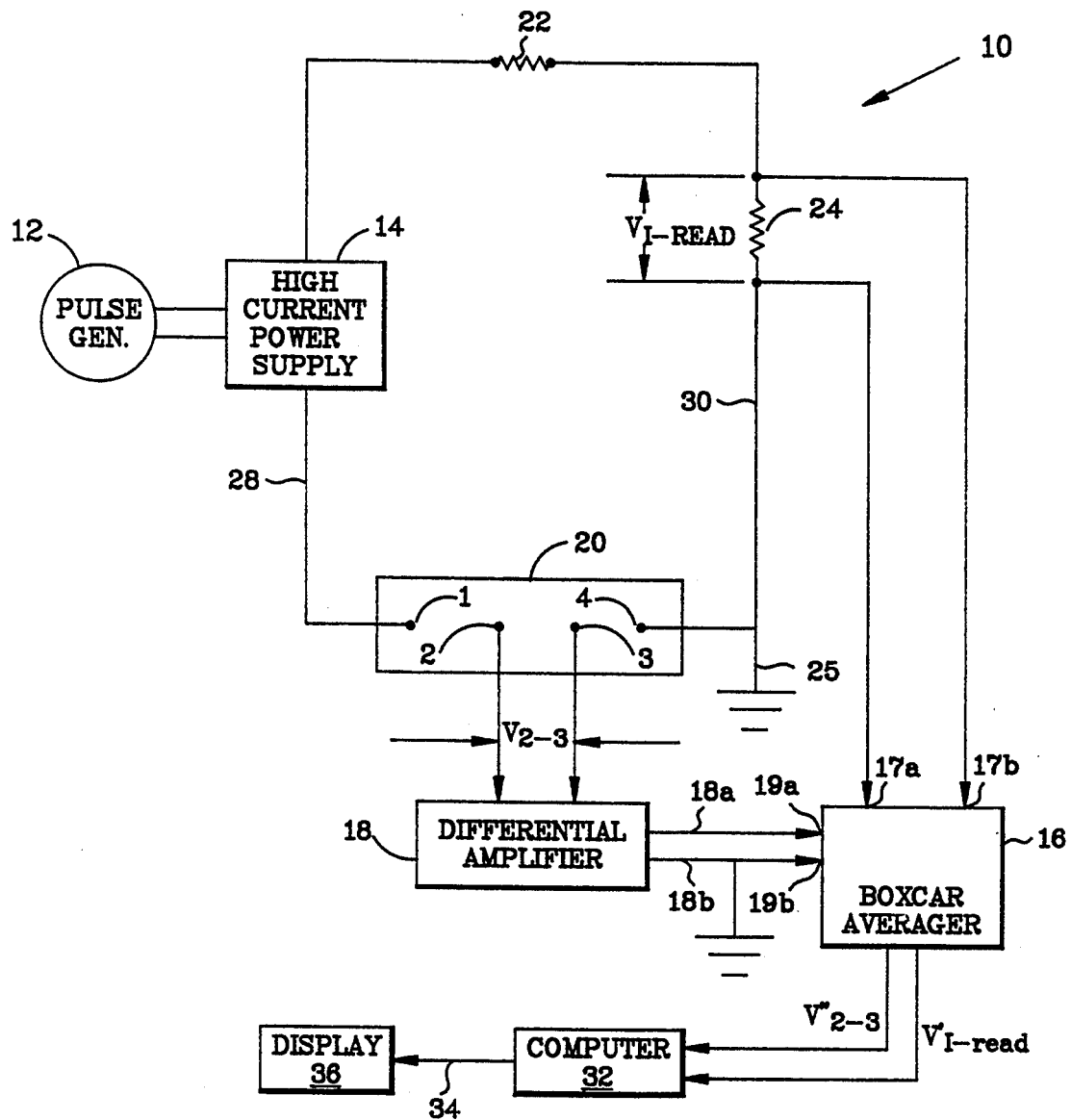
FIG. 2 is a schematic diagram of an example of a pulsed-DC circuit suitable for determining the granular nature of a superconducting material in accordance with the method of the present invention.

Referring now to FIG. 2, there is illustrated an example of one type of circuit 10 by which the method of the present invention may be implemented. Pulses produced by pulse generator 12, which may be a Tektronix PG505, are amplified by a high-current power supply 14, such as a Kepco BOP36-5M or Kepco ATE25-40M, depending on the current range. Current provided by power supply 14 is conducted through electrical contacts 1 and 4 made to superconductive sample 20, which is cooled, for example, by immersion in a liquid cryogen, not shown. The term "superconductive" refers to a material which is a superconductor under appropriate conditions. If power supply 14 is preferably operated in a constant voltage mode rather than a constant current mode ("constant" during the pulse interval), then current-limiting resistor 22 is preferably included in circuit 10 in series between power supply 14 and sample 20. The resistance, $R_{24}$ of resistor 24, in series between power supply 14 and sample 20, is selected so that the voltage across resistor 24 may be easily measured. Typical values of $R_{24}$ are 1 ohm for $I < 5$ A, and 10 milliohm for larger values of I. Resistor 24 may be a known precision resistor, or alternately $R_{24}$ may be accurately determined by a DC, 4-probe measurement, a well known technique by those skilled in this art. The power rating of resistors 24 and 22 must be sufficient to handle the pulsed current or currents conducted through sample 20. Contacts 2 and 3 on the sample 20 are used to detect the voltage, $V_{2-3}$, across the sample. The electrical resistance of the sample 20 can be determined in accordance with the relation: $V_{2-3}/I$, where I represents the current conducted through the sample, and $I=V_{I-read}/R_{24}$. When the sample 20 is in a superconducting state, $V_{2-3}$ is zero. $V_{2-3}$ increases from zero as the sample transitions into a non-superconducting, or nodal, state.

The voltage difference $V_{2-3}$ detected at the contacts 2 and 3 of the sample 20 is provided to differential amplifier 18, such as a PAR 126 lock-in amplifier, which provides an amplified voltage signal, $V'_{2-3}$, to inputs 19a and 19b of boxcar averager 16. The voltage $V_{I-read}$, read across resistor 24, is provided to inputs 17a and 17b during the boxcar gate pulse, which is set to be within the time frame of the current pulse (see FIG. 3, described below). The boxcar averager improves the signal-to-noise ratio of the voltage signals $V_{2-3}$ and $V_{I-read}$, and suitably scales $V'_{2-3}$ and $V_{I-read}$. Boxcar averager 16, may be implemented as a Princeton Applied Research (PAR) 162, and include two gated integrators (PAR 166).

Figure 3:
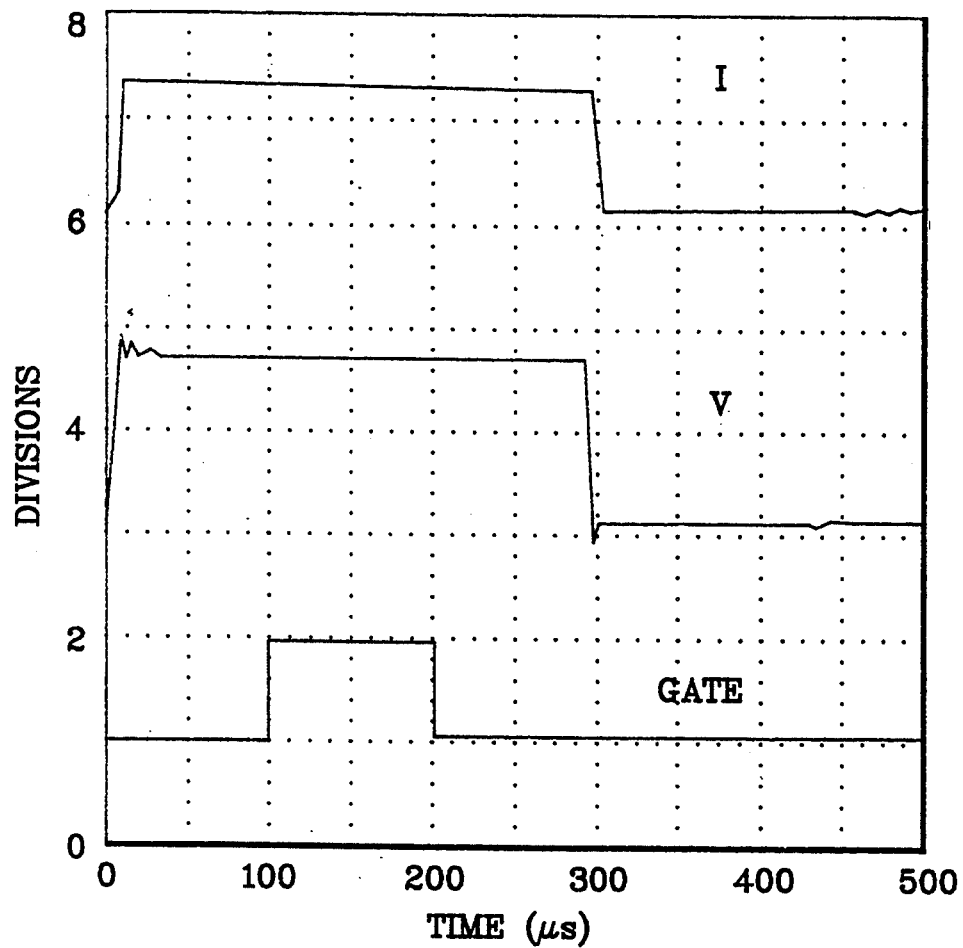
FIG. 3 is a representation of an oscilloscope screen illustrating the current (0.5 A/division), voltage (0.5 mV/division), and gate pulses associated with implementation of the method of the present invention as applied to a typical $YBa_2Cu_3O_7$ superconducting sample at a temperature of 84.9K.

By way of example, typical current pulse, I, sample voltage, $V_{2-3}$, and boxcar gate pulse waveforms for a $YBa_2Cu_3O_7$ sample at a temperature of 84.9K are shown in FIG. 3, in which the vertical scale is relative. The pulse waveforms are offset from zero for clarity. The current pulse amplitude of the current conducted through the sample is 1.5 A, as indicated by the curve labeled "I" in FIG. 3, and the voltage pulse amplitude is 2.1 mV, as represented by the curve labeled "V." The resistance of the $YBa_2Cu_3O_7$ at 84.9K temperature and at this current level is therefore (2.1 mV/1.5 A) or 14 mΩ. This superconducting material has a critical temperature of 92K (measured at the resistive transition mid-point), and a normal state (non-superconducting) resistance of 15.8 milliohms at 93K.

Referring again to FIG. 2, the location of circuit ground 25 in circuit 10 has been selected both for convenience and to minimize sample voltage noise. The positioning of circuit ground 25 between resistor 24 and one of the current contacts of sample 20 allows the use of the single-ended input (that is, input 17b is measured relative to ground at input 17a) of $V_{I-read}$ to boxcar averager 16. Proximity of the ground 25 to the sample voltage contacts 2 and 3 also helps prevent overloading of the differential amplifier 18. Note, however, that the location of circuit ground 25 requires that both the pulse generator 12 and differential amplifier 18 have a floating output. An isolation transformer, not shown, between pulse generator 12 and power supply 14 could be used to allow one side of the output of pulse generator 12 to be grounded. Alternatively, the circuit ground 25 could be placed elsewhere in the circuit 10 which would require $V_{I-read}$ to be measured differentially before being sent to the boxcar averager 16.

It has been found that current pulses with very sharp rise and fall times (<1 microsecond) may lead to voltage spikes which overshoot and undershoot, respectively, the expected sample voltages produced by the current pulses through sample 20. These spikes, originating from pulse generator 12, quickly relax back in an under-damped oscillation to the expected voltage levels. The spike amplitude increases as the resistance of sample 20 goes from the normal (non-superconducting) to the zero resistance state (superconducting), which tends to overload differential amplifier 18. The effect of the spikes is merely an artifact of the circuit parameters, having nothing to do with the superconductivity of sample 20, and occurs even if sample 20 is replaced by a short circuit. The deleterious effects of these voltage spikes are preferably minimized as follows. First, the gate of boxcar 16 is enabled so that the boxcar only "sees" the interior of the pulses, away from the spikes. Second, the rise and fall times of the pulses are increased to about 10 microseconds, which greatly reduces the spike amplitude. Finally, the spike amplitude may be greatly reduced by using twisted-pair current leads to contacts 1 and 4 of sample 20. Standard 50 ohm impedance coaxial cables are preferably used in those sections of the circuit 10 which are at room temperature.

In accordance with the method of the present invention, a rectangular (or, when non-zero rise and fall times are used, trapezoidal) pulse of typically a few hundred microseconds duration is preferably generated by pulse generator 12 and provided to high current power supply 14. A series of pulses, generated by pulse generator 12 at a typical frequency of a few Hertz, may also be used. The power supply 14 generates a constant amplitude current pulse, or series of pulses, which are conducted through superconductive material, or sample, 20 being maintained at a constant temperature below its critical temperature. The sample 20 is preferably maintained at this constant "sub-critical" temperature by immersion in a cryogenic fluid such as liquid nitrogen, or by thermally coupling it to a cooled, constant-temperature block sufficiently cooled to maintain the temperature of the sample below its critical temperature. The amplitude of the current pulse then is slowly increased (slow compared to the pulse repetition period) while the voltage difference $V_{2-3}$ is monitored. The voltage $V_{2-3}$, and hence resistance, of the sample is substantially zero until the current conducted through the sample exceeds the critical current of the sample, at which condition, $V_{2-3}$ (and sample resistance) rapidly increases with further increase of the current. For a granular superconductive sample 20, this critical current is believed to be characteristic of the intergranular weak links of the sample. The voltage $V_{2-3}$ continues to increase until the weak links are completely normal, where the resistance of the sample saturates to $R_1$, equal to the intergranular normal state resistance (the resistance of the now non-superconducting weak links between superconducting grains), $R_{inter}$. In the context of the method of the present invention, the term "saturation resistance" is understood to have one of the following two meanings, depending on the particular method of implementing the invention. In the preferred embodiment, the temperature of the sample is kept fixed while the current is varied. In this case, the saturation resistance refers to the condition where the rate of change of resistance with current, dR/dI, of the sample becomes substantially constant, where "R" represents the electrical resistance, and "I" represents the current through the sample 20. Alternatively, the method of the present invention may be implemented such that the current through the sample is fixed while the temperature is varied. In this latter case, the saturation resistance then refers to the condition when the rate of change of resistance with temperature, dR/dT, of the sample becomes substantially constant, as shown in FIG. 4, where "R"

represents the resistance, and "T" represents the temperature of the sample 20.

At this stage, the sample grains are superconducting, since they typically have a much higher critical current than the weak links. The sample resistance remains at this constant level while the current is further increased until the critical current of the grains is exceeded. The resistance then undergoes another sharp increase, eventually leveling off and saturating at $R_2$, equal to the total normal state resistance of the sample, $R_{total}$. $R_{total}$ is equal to the sum of the intragranular normal state resistance (the resistance of the now non-superconducting grains), $R_{intra}$, and the intergranular normal state resistance, $R_{inter}$. If the sample 20 is homogeneous, there is only one resistance saturation level, equal to $R_{total}$, since there are no weak links (non-superconducting material). In this case $R_1 = R_2$, $R_{inter} = 0$, and $R_{total} = R_{intra}$.

Figure 4:
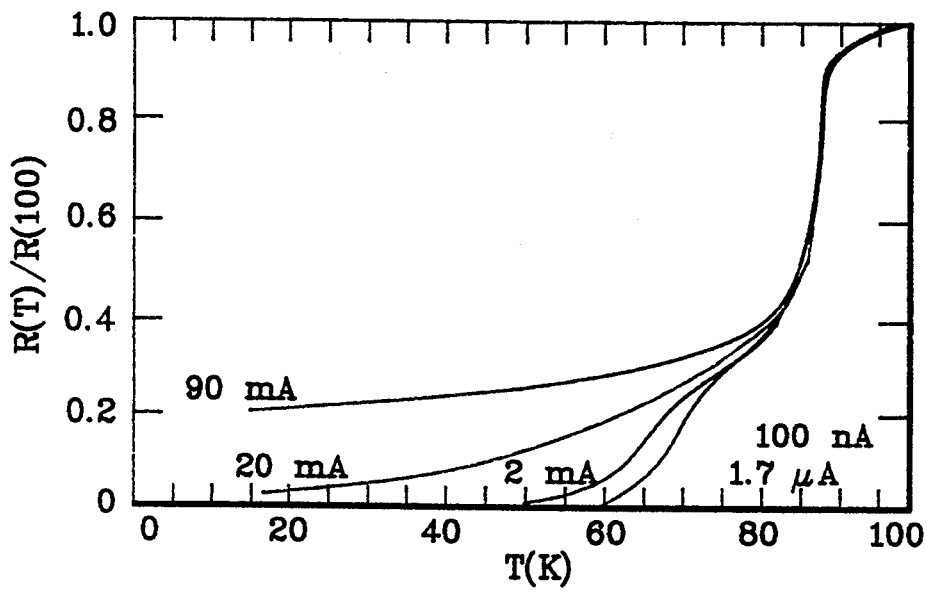
FIG. 4 is a graph of resistance, normalized to the resistance at a temperature of 100K, as a function of temperature for a granular thin film of $YBa_2Cu_3O_7$.

An example of electrical resistance saturation is shown in FIG. 4 for a single granular thin film of $YBa_2Cu_3O_7$ approximately 0.3 $\mu m$ thick. A family of resistance $[R(T)/R(100K)]$ versus temperature $[T(K)]$ curves, taken at various current amplitudes conducted through a single test sample, is plotted in FIG. 4. Resistance saturation is clearly shown in the temperature range of 15K to 60K, where the slopes of the curves become relatively flat as the current is increased. The curve at the far right of FIG. 4 is actually comprised of two overlapping curves resulting from a DC current (1.7 $\mu A$) and an AC current (100 nA). At 20K, the intergranular resistance of the $YBa_2Cu_3O_7$ sample film saturates to about 20% of R(100K) at a current of 90 mA.

Figure 5:
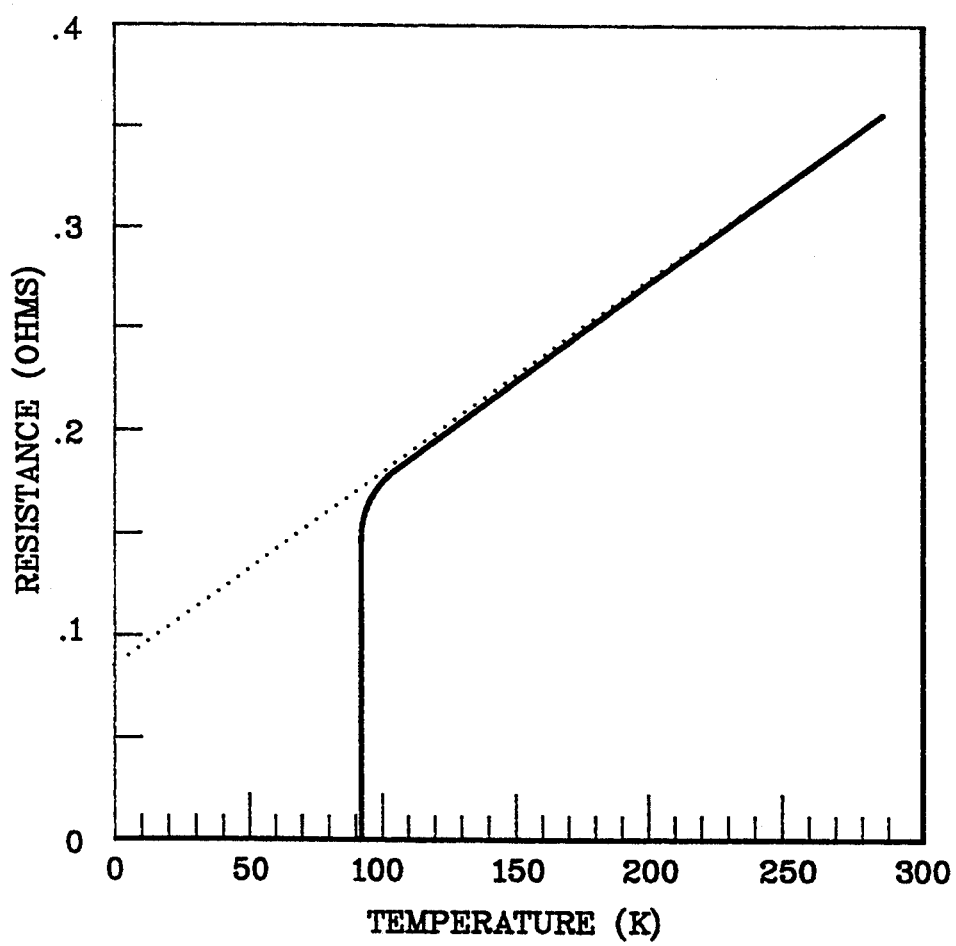
FIG. 5 is a graph of resistance versus absolute temperature (solid) for a sample of $YbBa_2Cu_3O_7$.

An alternative to determining $R_{total}$ at the temperature in question is to estimate its value from previous determinations of the normal state resistance (the resistance of sample 20 at temperatures above the critical temperature of sample 20) made as a function of temperature. The phrase "temperature in question" refers to the actual temperature of a superconductive test sample for which measurements are made to determine the granular nature of the sample. Such measurements of the normal state resistance could be made using low amplitude AC, DC, or pulsed currents. For example, FIG. 5 shows a plot of the resistance versus absolute temperature for a typical sample of $YbBa_2Cu_3O_7$, a high-temperature superconductor. The electrical resistance decreases from room temperature (near 300K) in an approximately linear fashion, then decreases suddenly to zero at the superconducting transition at a temperature of approximately 92K. The dotted line in FIG. 5 indicates the value that the resistance of the sample would have at a given temperature if the superconducting transition were suppressed, as by the passage of an electric current exceeding the critical current of the sample at a given temperature. Such dotted line represents an extrapolation of the normal state electrical resistance of the sample and can be used to estimate the normal state resistance that the sample would have if superconductivity were suppressed as by the passage of a large current. It should be noted that not all materials exhibit such a linear resistance behavior. However, a reasonable approximation to the normal state resistance may be made by analysis of the measured resistance characteristics above the transition temperature. Such analysis may be effectuated using well known curve fitting techniques which may be implemented by a suitable processing routine operated in computer 32. Extrapolation of the resistance, as described above, to the temperature in question (below the critical temperature of sample 20, where low current measurements would indicate that sample 20 has zero resistance) can provide a good estimate of $R_{total}$.

The saturation levels at $R_1$ and/or $R_2$ may, for example, be discerned by a computer 32, shown in FIG. 2, which receives the $V''_{2-3}$ and $V'_{I-read}$ output signals from the boxcar averager 16. Computer 32 implements a suitable processing routine for identifying voltage differences $V_{2-3}$ of sample 20 as a function of increasing current amplitude through the sample which are within a predetermined limit where the current is represented by $V_{I-read}/R_{24}$. The resistance of sample 20, $R_{20}$, may be determined by a processing routine implemented in the computer 32 in accordance with the equation: $R_{20} = V''_{2-3} R_{24}/V'_{I-read}$. The current amplitude, "I", may be determined by a processing routine also implemented in the computer 32 in accordance with the equation: $I = V'_{I-read}/R_{24}$. The absolute value of the difference, $\delta$, between the saturation levels $R_1$ and $R_2$ is then computed by the computer. The value $|\delta|$ is then compared to a predetermined limit, $\epsilon$. The value of $\epsilon$ is preferably very small, and is ultimately limited by the experimental error in measuring the resistance of sample 20.

In the case where $|\delta| \leq \epsilon$, the sample 20 has only one resistance saturation level, and therefore only one component to the normal state resistance of the sample 20, and one component making up the sample 20. Thus, where $|\delta| \leq \epsilon$, the sample has a generally homogeneous morphology. In the case where $|\delta| > \epsilon$, sample 20 has two resistance saturation levels, and therefore both intergranular and intragranular components to the total normal state resistance. Thus, where $|\delta| > \epsilon$, the sample has a granular morphology. The computer 32 may generate an output signal 34 which represents the morphology of the sample. Such output signal 34 may be provided to a suitable display 36, such as a printer, video monitor, or the like. For a given sample 20 then, the computer may, for example, output the message "HOMOGENEOUS" if $|\delta| \leq \epsilon$, or the message "GRANULAR" if $|\delta| > \epsilon$.

In summary, the pulsed-DC method of the present invention may be used to determine the granular or homogeneous nature of a superconductive material, or sample, by comparing the determined normal state resistance of the material to the known or estimated total normal state resistance. Such method includes the following steps:

1) conducting one or more substantially rectangular current pulses through sample 20 using pulse generator 12 and high current power supply 14;
2) maintaining the sample 20 at a constant temperature that does not exceed the critical temperature of sample 20, preferably by immersing the sample in a cryogenic liquid, such as liquid nitrogen;
3) determining the amplitude, I, of the current pulse through sample 20 by detecting the voltage, $V_{I-read}$, across the resistor 24, in series with the sample, while conducting the pulse, and then dividing $V_{I-read}$ by $R_{24}$;
4) determining the electrical resistance of the sample 20 by detecting the voltage difference $V_{2-3}$ across sample 20, detected at contacts 2 and 3, with differential amplifier 18 while conducting the current pulse;
5) increasing the amplitude of the current pulse until the resistance of sample 20 saturates, designated as $R_1$, i.e, where $V_{2-3}$ saturates, or becomes relatively constant as a function of increasing current amplitude, "I", represented by $I=V'_{I-read}/R_{24}$, and where the electrical resistance, $R_{20}$, of the sample 20 is represented by $R_{20}=V'_{2-3}R_{24}/V'_{I-read}$;

6) determining an electrical resistance difference, $|\delta|$, between $R_1$ and the known or estimated total normal state resistance $R_{total}$ of the sample, as for example, by using the computer 32 implementing a suitable processing routine;

7) generating a first output signal, preferably using the computer 32, if $|\delta| \leq \epsilon$, where $\epsilon$ represents a predetermined limit, corresponding to sample 20 having a homogeneous morphology; and 8) generating a second output signal, also preferably using the computer 32, if $|\delta| > \epsilon$, corresponding to sample 20 having a granular morphology.

This pulsed-DC method may also be used to determine the granular or homogeneous nature of a superconductive material, or sample, by comparing the normal state resistance of the sample to the total normal state resistance of the sample, and includes the following steps:

1) conducting one or more substantially rectangular current pulses through sample 20 using pulse generator 12 and high current power supply 14;

2) maintaining the sample 20 at a constant temperature that does not exceed the critical temperature of sample 20, preferably by immersing the sample in a cryogenic liquid, such as liquid nitrogen;

3) determining the amplitude of the current pulse through sample 20 by detecting the voltage, $V_{I-read}$, across the resistor 24, in series with the sample, while conducting the pulse, and then dividing $V_{I-read}$ by $R_{24}$;

4) determining the electrical resistance of the sample 20 by detecting the voltage difference $V_{2-3}$ across sample 20, detected at contacts 2 and 3, with differential amplifier 18 while conducting the current pulse;

5) increasing the amplitude of the current pulse until the resistance of sample 20 saturates, designated as $R_1$, i.e, where $V_{2-3}$ saturates, or becomes relatively constant as a function of increasing current amplitude, "I", represented by $I=V'_{I-read}/R_{24}$, and where the resistance, $R_{20}$ of the sample 20 is represented by $R_{20}=V'_{2-3}R_{24}/V'_{I-read}$;

6) further increasing the amplitude of the current pulse using the pulse generator 12 and high power current supply 14 until the electrical resistance of the superconductive sample 20 increases from the first saturation resistance, $R_1$, to a second saturated electrical resistance, $R_2$, where the second saturated electrical resistance is equal to the total normal state electrical resistance of the sample;

7) determining an electrical resistance difference, $|\delta|$, between $R_1$ and $R_2$ (the known or estimated total normal state resistance $R_{total}$ of the sample), as for example, by implementing a suitable processing routine in the computer 32;

8) generating a first output signal, preferably using the computer 32, if $|\delta| \leq \epsilon$, where $\epsilon$ represents a predetermined limit, corresponding to sample 20 having a homogeneous morphology; and 9) generating a second output signal, also preferably using the computer 32, if $|\delta| > \epsilon$, corresponding to sample 20 having a granular morphology.

Obviously, many modifications and variations of the present invention are possible in light of the above teachings. It is therefore to be understood that within the scope of the appended claims, the invention may be practiced otherwise than as specifically described.

We claim:

1. A method for determining the granular nature of a superconductive material, comprising the steps of:

conducting a substantially rectangular current pulse having an amplitude through said superconductive material, said superconductive material having a critical temperature;

maintaining the temperature of said superconductive material at a substantially constant temperature which does not exceed said critical temperature of said superconductive material;

determining said amplitude of said current pulse;

determining the electrical resistance, R, of said superconductive material resulting from conducting said current pulse through said superconductive material;

increasing said amplitude of said current pulse until said electrical resistance of said superconductive material becomes saturated;

determining an electrical resistance difference, $\delta$, between a saturated electrical resistance, $R_1$, of said saturated superconductive material and a total normal state electrical resistance of said superconductive material;

generating a first output signal if $|\delta| \leq \epsilon$, where $\epsilon$ represents a predetermined limit, where said first output signal corresponds to said superconductive material having a homogeneous microscopic morphology; and generating a second output signal if $|\delta| > \epsilon$, where said second output signal corresponds to said superconductive material having a granular microscopic morphology.

2. The method of claim 1 wherein:
said step of conducting includes conducting a series of current pulses through said superconductive material.

3. The method of claim 2 further including the step of averaging said electrical resistance differences over a predetermined number of said current pulses.

4. The method of claim 1 further including the step of determining said total normal state resistance of said superconductive material at said constant temperature.

5. The method of claim 4 wherein said step of conducting includes conducting a series of current pulses through said superconductive material.

6. The method of claim 5 further including the step of averaging said electrical resistance difference over a predetermined number of said current pulses.

7. A method for determining the granular nature of a superconductive material, comprising the steps of:

conducting a substantially rectangular current pulse through said superconductive material, said superconductive material having a critical temperature;

maintaining the temperature of said superconductive material at a substantially constant temperature which does not exceed said critical temperature of said superconductive material;

determining said amplitude of said current pulse;

determining the electrical resistance of said superconductive material resulting from conducting said current pulse through said superconductive material;

increasing said amplitude of said current pulse until said electrical resistance of said superconductive material becomes saturated at a first saturated electrical resistance, $R_1$;

further increasing said amplitude of said current pulse until said electrical resistance of said superconductive material increases from said first saturated electrical resistance, $R_1$, to a second saturated electrical resistance, $R_2$, said second saturation electrical resistance being equal to the total normal state electrical resistance of said superconductive sample;

determining an electrical resistance difference, $\delta$, between $R_1$ and $R_2$;

generating a first output signal if $|\delta| \leq \epsilon$, where $\epsilon$ represents a predetermined limit, where said first output signal corresponds to said superconductive material having a homogeneous morphology; and generating a second output signal if $|\delta| > \epsilon$, where said second output signal corresponds to said superconductive material having a granular morphology.

8. The method of claim 7 wherein said step of conducting includes conducting a series of current pulses through said superconductive material.

9. The method of claim 8 further including the step of averaging said electrical resistance differences over a predetermined number of said pulses.

* * * * *